US012681328B2

(12) United States Patent
Sayag

(10) Patent No.: US 12,681,328 B2
(45) Date of Patent: Jul. 14, 2026

(54) METHOD FOR SIMULATING OPTICAL PRODUCTS

(71) Applicant: ACEP FRANCE, Paris (FR)

(72) Inventor: Jean-Philippe Sayag, Paris (FR)

(73) Assignee: ACEP FRANCE, Paris (FR)

( * ) Notice: Subject to any disclaimer, the term of this patent is extended or adjusted under 35 U.S.C. 154(b) by 288 days.

(21) Appl. No.: 18/562,978

(22) PCT Filed: Jun. 17, 2022

(86) PCT No.: PCT/EP2022/066604
§ 371 (c)(1),
(2) Date: Nov. 21, 2023

(87) PCT Pub. No.: WO2022/263652
PCT Pub. Date: Dec. 22, 2022

(65) Prior Publication Data
US 2024/0210730 A1        Jun. 27, 2024

(30) Foreign Application Priority Data

Jun. 18, 2021    (FR) .................................. FR2106475

(51) Int. Cl.
G02C 7/02          (2006.01)
A61B 3/04          (2006.01)
A61B 90/00         (2016.01)

(52) U.S. Cl.
CPC ................ G02C 7/028 (2013.01); A61B 3/04 (2013.01); A61B 2090/365 (2016.02)

(58) Field of Classification Search
None
See application file for complete search history.

(56) References Cited

U.S. PATENT DOCUMENTS

| | | | |
|---|---|---|---|
| 8,823,742 B2 | 9/2014 | Kweon | |
| 9,717,404 B1 * | 8/2017 | Brauner ................... | G02C 7/02 |
| 2010/0079722 A1 * | 4/2010 | Guilloux ............... | G02C 7/065 |
| | | | 700/103 |
| 2015/0055086 A1 * | 2/2015 | Fonte ..................... | G02C 7/024 |
| | | | 700/98 |

(Continued)

FOREIGN PATENT DOCUMENTS

| | | |
|---|---|---|
| EP | 2899585 A1 | 7/2015 |
| FR | 3067151 A1 | 12/2018 |

(Continued)

OTHER PUBLICATIONS

International Search Report and Written Opinion issued on Jul. 25, 2022, in corresponding International Application No. PCT/EP2022/066604, 17 pages.

*Primary Examiner* — Sharrief I Broome
*Assistant Examiner* — Journey F Sumlar
(74) *Attorney, Agent, or Firm* — Maier & Maier, PLLC

(57) ABSTRACT

A method for simulating optical lenses in augmented reality using a mobile apparatus including at least an input peripheral and a display peripheral, the method includes at least, a capture phase a data acquisition phase while the user is looking at an object in the environment, and a simulation phase performed by at least a processing unit allowing a virtual lens to be produced and superposed on at least an image of a user's environment.

9 Claims, 1 Drawing Sheet

(56) References Cited

U.S. PATENT DOCUMENTS

| 2016/0035133 | A1* | 2/2016 | Ye | G06T 15/60 |
| | | | | 345/419 |
| 2017/0188813 | A1 | 7/2017 | Arnold et al. | |
| 2020/0219326 | A1 | 7/2020 | Goldberg et al. | |
| 2021/0142566 | A1* | 5/2021 | Dehais | G06T 15/20 |

FOREIGN PATENT DOCUMENTS

| WO | 2017134275 | A1 | 8/2017 |
| WO | 2020243771 | A1 | 12/2020 |

* cited by examiner

[Fig. 1]

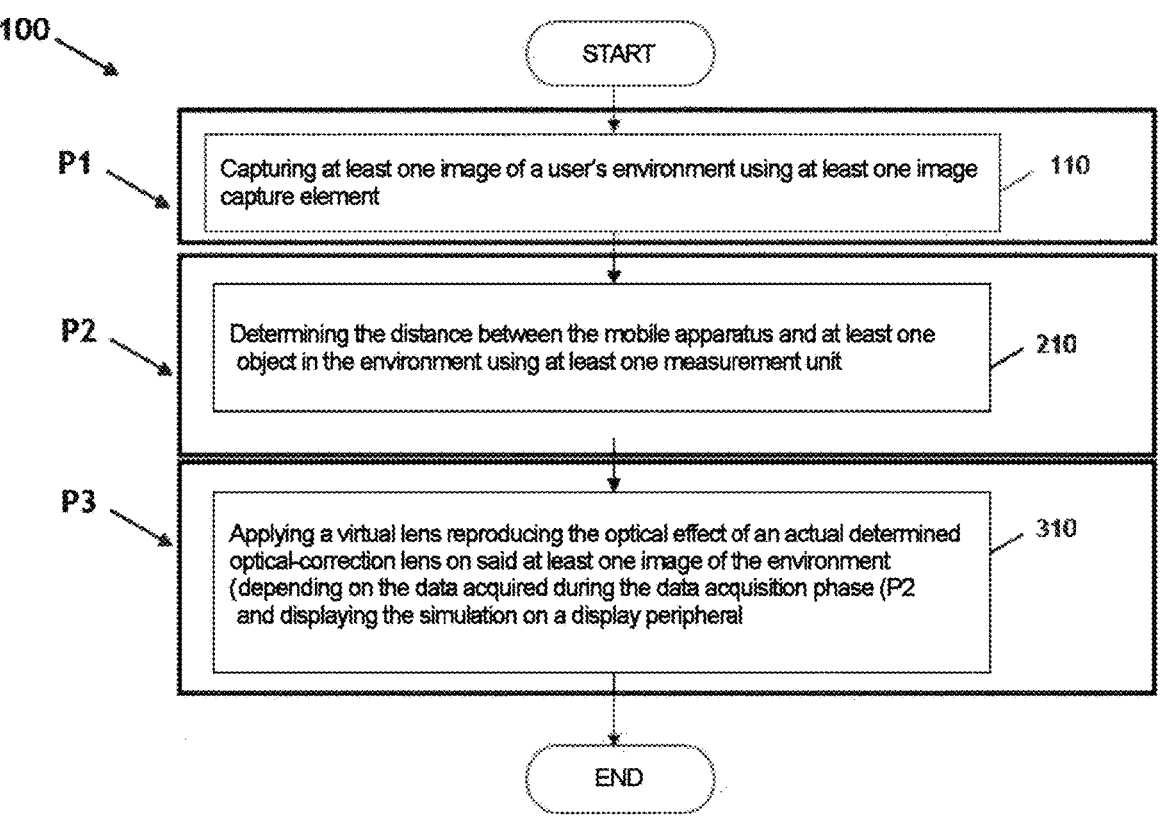

100

START

P1 — Capturing at least one image of a user's environment using at least one image capture element — 110

P2 — Determining the distance between the mobile apparatus and at least one object in the environment using at least one measurement unit — 210

P3 — Applying a virtual lens reproducing the optical effect of an actual determined optical-correction lens on said at least one image of the environment (depending on the data acquired during the data acquisition phase (P2 and displaying the simulation on a display peripheral — 310

END

[Fig. 2]

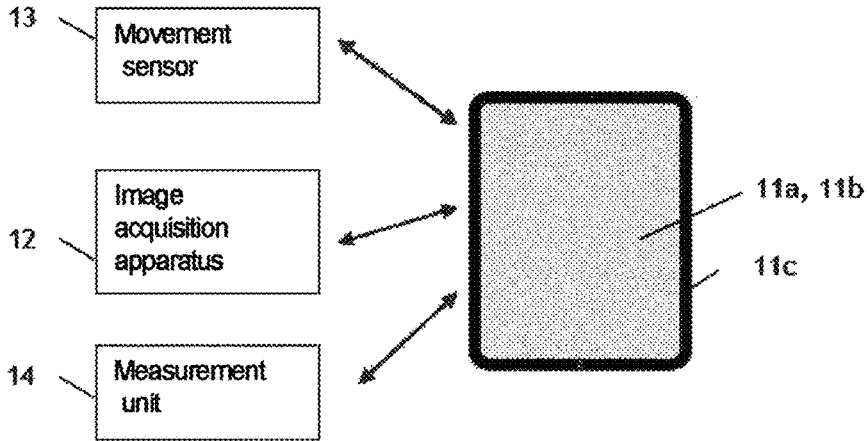

13 — Movement sensor

12 — Image acquisition apparatus

14 — Measurement unit 11a, 11b

11c

METHOD FOR SIMULATING OPTICAL PRODUCTS

FIELD

The present invention relates to the field of optics and more particularly the field of trying on lens-type optical products, using augmented reality.

BACKGROUND

In the field of trying on optical products, it is known to use the information concerning an individual's eyesight contained in his prescription to select correction lenses appropriate to his eyesight and manufacture them for try-on. The drawback of this type of try-on lies in the fact that if the selected optical product is not suitable for the patient, it is discarded and another optical product must be manufactured again.

Tin order to overcome this drawback, a method for simulating lenses in augmented reality is well known, which, using a tablet, allows a user to simulate the effect of a lens on an image of the user's environment captured in real time. However, this type of method does not allow realistically simulate the effect of a lens with power variation, that is to say a lens characterised by the fact that it offers, over its entire surface, different powers dedicated to different viewing distances. Indeed, this simulation system does not take into account the distance of the different elements of the environment with the tablet and therefore does not allow reproduce as faithfully as possible the 3D perception of the visual field perceived depending on the design of the represented lens. Thus, this type of system provides a simulation experience that is not very representative of reality for a wearer, in particular in the case of the simulation of progressive lenses intended to correct a vision called "near" vision and a vision called "far" vision.

SUMMARY

The aim of the present invention is therefore to overcome the previously mentioned drawbacks and to propose a method for simulating optical lenses based on augmented reality allowing a realistic reproduction of the effect of optical lenses on the visual perception of an environment composed of elements located at different distances from the user.

In accordance with the invention, a method for simulating optical lenses in augmented reality using a mobile apparatus including at least one input peripheral and one display peripheral, said method being remarkable in that it includes at least, one capture phase (P1) including at least the following step:

a1) Capturing at least one image of a user's environment using at least one image capture element:

one data acquisition phase (P2) including at least the following step:

b1) Determining the distance between the mobile apparatus and at least one object in the environment using at least one measurement unit;

and one simulation phase (P3) implemented by said at least one processing unit, including at least the following step:

c1) Applying a virtual lens reproducing the optical effect of an actual determined optical-correction lens, on said at least one image of the environment, depending on the data acquired during the data acquisition phase (P2) and displaying the simulation on a display peripheral.

The so-called "mobile apparatus" is a portable computing apparatus which can be used autonomously. This is, for example, a tablet, a smartphone or a laptop.

The so-called "user" is the individual using the mobile apparatus for the purpose of obtaining a simulation of corrective lenses, it could be, for example, a patient for whom a corrective product has been designed or even an optician.

The so-called "lens" is a transparent optical orthosis, very thin and concave, which is placed on the cornea of the eye to correct vision defects. Reference is made to "lens type" in order to designate lenses offering different types of optical corrections, which have different types of coatings or tints.

The so-called "input peripheral" is peripheral computer equipment allowing providing data to an information processing system such as a computer. This is for example a keyboard, a mouse, a touch screen (the touch screen can be considered as an input and output peripheral at the same time). This peripheral can be integrated into the mobile apparatus therefore become an integral part of the device or transmit its data thereto by means of a wired or wireless connection.

The so-called "display peripheral" is an output device allowing information to be displayed, it is for example the screen of the mobile apparatus or a screen which receives data from the mobile apparatus through a wired or wireless connection.

The so-called "image capture element" is a photo or video camera type apparatus. This apparatus can be integrated into the mobile apparatus (for example, smartphone or tablet camera) or be independent and connected to the mobile apparatus.

The so-called "measurement unit" is an instrument or application allowing the distance measurement. This instrument can be integrated into the mobile apparatus or transmit its data thereto by means of a wired or wireless connection.

The so-called "processing unit" is all elements of the mobile apparatus (processor, memory . . . ) used for the storage and exploitation of information on the environment and the eyesight of a future wearer.

The so-called "virtual lens" is an image filter created in augmented reality and allowing creating optical effects on an image (creating blurred areas for example, changing the colour of the image, etc. . . . )

Preferably, during step c1, said virtual lens is selected from a pre-existing database of lenses with different modifiable mappings or is completely created as required.

The so-called "mapping" of a lens the manner in which the different optical-correction power areas are arranged on the surface thereof.

Advantageously, during the simulation phase (P3), the user chooses to simulate a lens: multifocal, with power variation, progressive, digressive, with specific positioning, for suppression, of myopia progression, with fixed or gradient or bi-gradient tint, photochromic, polarising, coating, or anti-fatigue.

Preferably, the data acquisition phase (P2) includes a step b2 which takes place during the observation of the environment by a wearer through the display peripheral of the mobile apparatus and which consists in determining the movements of the wearer's head, and the distance between the wearer and the mobile apparatus using a movement sensor.

The so-called "wearer" is a patient for whom the lenses are intended.

Even more preferentially, the determination of the movements at the wearer's head consists in detecting the movements of the wearer's face and eyes relative to the mobile apparatus using a movement sensor.

Advantageously, step a1 is a step of capturing in real time at least one image of a user's environment using at least one image capture element.

Preferably, in step b1, the measurement unit allowing determining the distance between the mobile apparatus and the object is a telemetric device or application.

The so-called "telemetric device or application" is a device and an application allowing the distance of an object to be measured by computer means (applications based on the calculation of distance following the capture of an image of the object for example), which is optical (laser telemetry for example), acoustic (sonar for example) or radio (radar for example).

Advantageously, the is a laser, ultrasonic, acoustic measuring rangefinder or a remote measuring application.

Preferably, at least the image capture element, and the measurement unit are integrated into the mobile apparatus.

Advantageously, the mobile apparatus is a tablet or a smartphone and the display peripheral is the screen of said tablet or of said smartphone.

Preferably, in step c1, the simulation is displayed on the display peripheral of the mobile apparatus.

BRIEF DESCRIPTION OF THE FIGURES

Other advantages and feature will become clearer from the following description of a mode of execution of a method according to the invention, with reference to the appended figures in which:

FIG. 1 is a flowchart of the steps of the method in accordance with the invention, FIG. 2 is a schematic view of one embodiment of a system for implementing the method in accordance with the invention.

DETAILED DESCRIPTION

In accordance with FIGS. 1 and 2, a method 100 for simulating optical lenses in augmented reality using a mobile apparatus 11 is therefore described, including at least one input peripheral 11a and one display peripheral 11b, said method 100 being remarkable in that it includes at least, one capture phase (P1) including at least the following step:

a1) Capturing at least one image of a user's environment using at least one image capture element 12, 110;

one data acquisition phase (P2) including at least the following step:

b1) Determining the distance between the mobile apparatus 11 and at least one object in the environment using at least one measurement unit 14, 210;

and one simulation phase (P3) implemented by said at least one processing unit 11c of the mobile apparatus, including at least the following step:

c1) Applying a virtual lens reproducing the optical effect of an actual determined optical-correction lens, on said at least one image of the environment, depending on the data acquired during the data acquisition phase (P2) and displaying the simulation on a display peripheral, 310;

The mobile apparatus 11 could be a tablet, a smartphone or a laptop. Regardless of the mobile apparatus 11, the display peripheral 11b will be the screen of the mobile apparatus 11 or an independent screen connected to the mobile apparatus 11 by a wired or wireless connection (for example, USB cable connection, Bluetooth connection . . . ). If the mobile apparatus 11 is a tablet or a smartphone, the input peripheral 11a will preferably be a touch screen. If the mobile apparatus 11 is a laptop PC, the input peripheral 11a will be a keyboard and/or a mouse and/or a touch screen. This input peripheral 11a will aim at allowing selecting the different types of lenses to be simulated or at creating lenses with new mappings. It could also be used to enter the optical correction of the product for the simulation.

The image capture element 12 is a photo or video camera type apparatus which can be integrated into the mobile apparatus (camera of a tablet or smartphone for example) or connected thereto by a wired or wireless connection (for example, USB cable connection, Bluetooth connection . . . ). This image capture element 12 aims at capturing an image of the environment and transmitting this image to the display peripheral 11b of the mobile apparatus 11. The captured image could be a mage taken in real time or offline.

The processing unit 11c then creates a custom lens image by processing all data acquired during the data acquisition phase P2 and by taking into account a certain amount of information relating to general manufacturing of optical lenses previously stored on the mobile apparatus 11. Taking into account the distance environment-mobile apparatus 11, is a determining factor in the accuracy of the simulation of the lens. Indeed, this allows reproducing as faithfully as possible what can be perceived by an ametropic or emmetropic eye equipped with a device for compensating for its ametropia and/or presbyopia. Any lens with power variation offers, over its entire surface, a mapping of different powers dedicated to viewing distances which can be comprised between infinity and 30 cm. This implies that in the user's visual field, any object perceived through the optical zone which does not correspond to its position of remoteness will be perceived blurry. The user is therefore obliged to modify his gaze direction in order to use the optical zone which corresponds to the remoteness from the targeted object. For example, in the case of a progressive lens, if the subject looks down to go down a staircase, he uses the optical zone reserved for near vision and the targeted steps will be seen blurry. Another example: If a subject looks into the distance with a progressive lens, the objects located on the periphery of his horizontal visual field will be perceived blurry due to the iso-astigmatisms present laterally on the surface of said progressive lens.

The advantage of this distance measurement (step b1), is therefore to reproduce as faithfully as possible the 3D perception of the visual field perceived depending on the mapping of the selected lens and thus demonstrate the existing differences between different types of lenses.

This lens developed in augmented reality is superposed on the image of the environment captured by the image capture element 12.

The user looking at the display peripheral then sees exactly what he would see if he was wearing real corrective lenses. Following this simulation, if the eye product is suitable, the manufacturing of the product can be launched.

Preferably, during step c1, said virtual lens is selected from a pre-existing database of lenses with different modifiable mappings or is completely created as required. The user can select from a database a lens with a "typical" mapping, the processing unit 11c will then generate a particular virtual optical-correction lens according to this mapping: for example, progressive lens. The user will be able, if necessary, to modify the mapping of a lens from the database or choose to create a new lens or a new virtual lens with a custom mapping in order to meet the needs of the future wearer.

Advantageously, during the simulation phase (P3), the user can choose to simulate a lens: multifocal, with power variation, progressive, digressive, with specific positioning, for suppression, of myopia progression, with fixed or gradient or bi-gradient tint, photochromic, polarising, coating, or anti-fatigue.

Preferably, the data acquisition phase (P2) includes a step b2 which takes place during the observation of the environment by a wearer through the display peripheral 11*b* of the mobile apparatus 11 and which consists in determining the movements of the wearer's head, and the distance between the wearer and the mobile apparatus 11 using a movement sensor 13.

During the data acquisition phase (P2), the visual behaviour of the wearer relative to the image of the environment that he observes on the display peripheral 11*b* is determined and recorded, the distances between it and the mobile apparatus 11 and between the mobile apparatus 11 and an object in the environment are measured. These data will be transmitted to the processing unit 11*c* which will record and interpret them in order to determine the optical correction necessary for the wearer and in order to simulate a lens corresponding to this correction.

Even more preferably, the determination of the movements at the wearer's head consists in detecting the movements of the wearer's face and eyes relative to the mobile apparatus 11 using a movement sensor 13. The movement sensor 13 can take the form of any type of sensor which allows detecting the movement. Preferably, it will be an optical sensor which could be part of the mobile apparatus 11 or be connected thereto by a wired or wireless connection. The sensor 13 allows detecting the movements of a wearer who observes the environment while holding the mobile apparatus 11 in his hands. It can detect, for example, that the wearer approaches or moves back the mobile apparatus 11, that the wearer moves the apparatus 11 upwards, downwards, left or right or even determine the distance between the wearer and the mobile apparatus 11 using an acceleration sensor.

Advantageously, step a1 is a step of capturing in real time at least one image of a user's environment using at least one image capture element 12.

Preferably, in step b1, the measurement unit 14 allowing determining the distance between the mobile apparatus 11 and the object is a telemetric device or application. The so-called "telemetric device or application" is a device and an application allowing the distance of an object to be measured by computer means (applications based on the calculation of distance following the capture of an image of the object for example), which is optical (laser telemetry for example), acoustic (sonar for example) or radio (radar for example).

If the mobile apparatus 11 is a tablet or a smartphone, the measurement unit 14 could be a remote measurement application such as for example "Mapulator" or "EasyMeasure" on Android and iOS. "Easy measure" allows accurately measuring, using an image capture apparatus 12 in real time and augmented reality, several distances including the distance between the mobile apparatus 11 and an object. In a particular embodiment, the measurement unit 14 will be a laser rangefinder connected to the mobile apparatus 11 by a wired or wireless connection and whose operation will be as follows: I will project a laser beam onto an object in the environment which will in turn return the light ray, the rangefinder will then calculate the phase shift between the emission and the reception:

Preferably, the mobile apparatus 11 equipped with LiDAR (Light Detection and Ranging) technology. LiDAR technology allows a detection and a distance estimation by light or laser. This remote measurement technology is possible thanks to the analysis of the properties of a light beam returned to its emitter (mobile apparatus 11). LiDAR uses light to measure the distance using invisible pulsed green spectrum lasers. These pulses (which occur thousands of times per minute) measure the time required for the light to return to the sensor. In doing so, it creates an "image" of the environment in front of the scanner.

Advantageously, the measurement unit 14 is a laser, ultrasonic, acoustic measuring rangefinder or a remote measuring application.

Preferably, the image capture element 12, and the measurement unit 14 are integrated into the mobile apparatus 11. The term "integrated" here means that the mobile apparatus 11 has control of these different elements, either these elements are an integral part of the body/casing the mobile apparatus 11, or they are external thereto (they are not part of the casing of the mobile apparatus 11), but can only operate under the control of the mobile apparatus 11. In this manner, the simulation is easier to set up. The movement sensor 13 can also be integrated into the mobile apparatus 11. Obviously, if movement sensors 13, image capture elements 12 and/or measurement units 14 different from those integrated into the mobile apparatus 11 are necessary, it is entirely possible to use the appropriate apparatus(es) by connecting them via a wired or wireless connection to the mobile apparatus 11.

Advantageously, the mobile apparatus 11 is a tablet or a smartphone and the display peripheral 11*b* is the screen of said tablet or said smartphone. An apparatus which is powerful enough to support this type of simulation will be chosen from the existing mobile apparatuses 11. For example, an iPad type tablet will be chosen. On the tablet or the smartphone, the image capture element 12 and the measurement unit 14 will preferably be at the rear of the apparatus 11, while the image sensor will rather be at the front on the side of the screen.

Even more advantageously, the simulation is displayed on the display peripheral 11*b* of the mobile apparatus 11.

Finally, it goes without saying that the examples of methods 100 in accordance with the invention which have just been described are only particular illustrations, in no way limiting of the invention.

The invention claimed is:

1. A method for simulating optical lenses in augmented reality using a mobile apparatus including at least one input peripheral and one display peripheral, said method comprising:

one capture phase including at least the following step:

a1) capturing at least one image of a user's environment using at least one image capture element;

one data acquisition phase including at least the following step:

b1) determining the distance between the mobile apparatus and at least one object in the environment using at least one measurement unit;

and one simulation phase (P3) implemented by at least one processing unit of the mobile apparatus, including at least the following step:

c1) applying a virtual lens reproducing the optical effect of an actual determined optical-correction lens, on said at least one image of the environment, depending on the data acquired during the data acquisition phase and displaying the simulation on a display peripheral;
   wherein during step c1, said virtual lens is selected from a pre-existing database of lenses with different modifiable mappings or is created with a custom mapping.

2. The method according to claim 1, wherein during the simulation phase, the user chooses to simulate a lens: multifocal, with power variation, progressive, digressive, with specific positioning, for suppression, of myopia progression, with fixed or gradient or bi-gradient tint, photochromic, polarising, coating, or anti-fatigue.

3. The method according to claim 1, wherein the data acquisition phase includes a step b2 which takes place during the observation of the environment by a wearer through the display peripheral of the mobile apparatus and which consists in determining the movements of the wearer's head, and the distance between the wearer and the mobile apparatus using a movement sensor.

4. The method according to claim 3, wherein, the determination of the movements at the wearer's head consists in detecting the movements of the wearer's face and eyes relative to the mobile apparatus using a movement sensor.

5. The method according to claim 1, wherein step a1 is a step of capturing in real time at least one image of a user's environment using at least one image capture element.

6. The method according to claim 1, wherein, in step b1, the measurement unit allowing determining the distance between the mobile apparatus and the object is a telemetric device or application.

7. The method according to claim 6, wherein the measurement unit is a laser, ultrasonic, acoustic measuring rangefinder or a remote measuring application.

8. The method according to claim 1, wherein, at least the image capture element, and the measurement unit are integrated into the mobile apparatus.

9. The method according to claim 1, wherein the mobile apparatus is a tablet or a smartphone and in that the display peripheral is the screen of said tablet or of said smartphone.

*   *   *   *   *